United States Patent
Jeon et al.

(10) Patent No.: US 9,655,878 B2
(45) Date of Patent: May 23, 2017

(54) COMPOSITION COMPRISING COUMESTROL OR A BEAN EXTRACT CONTAINING COUMESTROL

(71) Applicant: AMOREPACIFIC CORPORATION, Seoul (KR)

(72) Inventors: Hee Y. Jeon, Gyeonggi-do (KR); Hyun Jung Shin, Seoul (KR); Dae Bang Seo, Gyeonggi-do (KR); Hyeon Ju Yeo, Seoul (KR); Sang Jun Lee, Gyeonggi-do (KR)

(73) Assignee: AMOREPACIFIC CORPORATION, Seoul (KR)

( * ) Notice: Subject to any disclaimer, the term of this patent is extended or adjusted under 35 U.S.C. 154(b) by 25 days.

(21) Appl. No.: 14/200,079

(22) Filed: Mar. 7, 2014

(65) Prior Publication Data

US 2014/0187622 A1  Jul. 3, 2014

Related U.S. Application Data

(62) Division of application No. 13/637,966, filed as application No. PCT/KR2011/002233 on Mar. 31, 2011.

(30) Foreign Application Priority Data

Mar. 31, 2010  (KR) .................. 10-2010-0029220

(51) Int. Cl.

| A61K 31/343 | (2006.01) |
|---|---|
| A61K 31/35 | (2006.01) |
| A61K 36/48 | (2006.01) |
| A61K 31/366 | (2006.01) |

(52) U.S. Cl.
CPC ............ *A61K 31/35* (2013.01); *A61K 31/366* (2013.01); *A61K 36/48* (2013.01)

(58) Field of Classification Search
CPC .................................................... A61K 31/343
See application file for complete search history.

(56) References Cited

U.S. PATENT DOCUMENTS

2005/0032882 A1* 2/2005 Chen .............................. 514/456
2012/0289714 A1* 11/2012 Jeon et al. .................... 549/279

FOREIGN PATENT DOCUMENTS

| CN | 1984648 A | 6/2007 |
|---|---|---|
| KP | 1020020059330 A | 7/2002 |
| KR | 10-0701269 B1 | 3/2007 |
| KR | 10-0706279 B1 | 4/2007 |
| WO | WO 01/41751 A2 | 6/2001 |
| WO | WO 03/075943 A2 | 9/2003 |
| WO | WO-2005/053724 | 6/2005 |

OTHER PUBLICATIONS

Sohrabji et al., Hormone replacement: therapeutic strategies in the treatment of Alzheimer's disease and ageing-related cognitive disorders, Expert Opinion on Therapeutic Patents, 1997, vol. 7, pp. 611-629.*
Gelinas et al., Neuroprotective Effect of Estradiol and Phytoestrogens on MPP-Induced Cytotoxicity in Neuronal PC12 Cells, Journal of Neuroscience Research, 2002, vol. 70, 90-96.*
X. Hao et al., "Analysis of Coumestrol Content in Soybeam," Journal of Beijing University of Agriculture, vol. 23, No. 3, pp. 7-9, Jul. 2008.
Bhathena et al., "Beneficial role of dietary phytoestrogens in obesity and diabetes," Am J Clin Nutri, 2002, 76, 1191-1201.
Schoenroth et al., "The effect of the phytoestrogen coumestrol on the NZB/W F1 murine modle of systemic lupus," *Journal of Autoimmunity*, 23 (2004) 323-332.
Gélinas et al., "Neuroprotective Effect of Estradiol and Phytoestrogens on MPP$^+$-Induced Cytotoxicity in Neuronal PC12 Cells," *Journal of Neuroscience Research*, 70:90-96 (2002).
González-Lamothe et al., "Plant Antimicrobial Agents and Their Effects on Plant and Human Pathogens," *Int. J. Mol. Sci.* 2009, 10, 3400-3419.
Cyr et al., "Estrogenic modulation of brain activity: implications for schizophrenia nad Parkinson's disease," *Revue de psychatrie & de neuroscience*, vol. 27, No. 1, 2002, pp. 12-26.
*Phytoestrogens and Human Health*, Shanghai Journal of Preventive Medicine, 2007, vol. 19, No. 7, pp. 359-361.
Journal of Anhui Agri. Sci., 2006, vol. 34, No. 10, pp. 2038-2039.

* cited by examiner

*Primary Examiner* — Rosanne Kosson
(74) *Attorney, Agent, or Firm* — Blank Rome LLP

(57) ABSTRACT

The present invention relates to a composition which comprises as an active ingredient coumestrol or a bean extract containing coumestrol, whereby adipocyte differentiation is inhibited, the immune system of the body is improved, toxic substances are purged, and neurodegenerative disorders are prevented or improved.

6 Claims, 1 Drawing Sheet

COMPOSITION COMPRISING COUMESTROL OR A BEAN EXTRACT CONTAINING COUMESTROL

CROSS-REFERENCE TO RELATED APPLICATIONS

The present application is a divisional of U.S. patent application Ser. No. 13/637,966, filed Sep. 27,2012, which entered the U.S. national stage from PCT Application Ser. No. PCT/KR2011/002233, filed Mar. 31, 2011, which claims priority to KR 10-2010-0029220, filed Mar. 31,2010, the entirety of which are incorporated herein by reference.

TECHNICAL FIELD

The present disclosure relates to a composition comprising coumestrol or a bean extract comprising coumestrol.

BACKGROUND ART

Bean is of great nutritional value and contains various physiologically active and functional substances. Especially, since the phytoestrogens contained in bean are similar to the estrogen of mammals including human in structure, they have the effect of preventing chronic diseases such as hormonal disorders. The phytoestrogens include in general isoflavone, coumestan and lignan.

SUMMARY OF THE INVENTION

Disclosure

Technical Problem

The present disclosure is directed to providing a composition for inhibiting differentiation of adipocytes, enhancing immunity, detoxifying toxic substances, and preventing or improving degenerative neurological disorders, comprising coumestrol or a bean extract comprising coumestrol as an active ingredient.

Technical Solution

In an aspect, the present disclosure provides a composition for inhibiting differentiation of adipocytes comprising coumestrol or a bean extract comprising coumestrol as an active ingredient.

In another aspect, the present disclosure provides a composition for enhancing immunity comprising coumestrol or a bean extract comprising coumestrol as an active ingredient.

In another aspect, the present disclosure provides a composition for detoxifying toxic substances comprising coumestrol or a bean extract comprising coumestrol as an active ingredient.

In another aspect, the present disclosure provides a composition for preventing or improving degenerative neurological disorders comprising coumestrol or a bean extract comprising coumestrol as an active ingredient.

Advantageous Effects

The composition according to an embodiment of the present disclosure, which comprises coumestrol or a bean extract comprising coumestrol as an active ingredient, has the effect of inhibiting differentiation of adipocytes, enhancing immunity, detoxifying toxic substances, and preventing or improving degenerative neurological disorders. The composition is useful in the field of food or medicine.

DETAILED DESCRIPTION OF THE INVENTION

Mode for Invention

Figure 1:
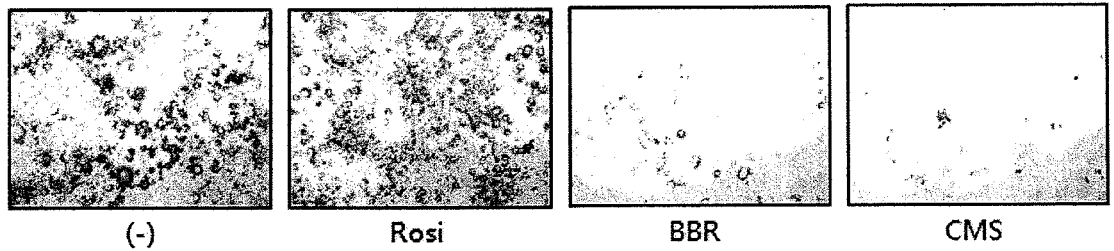
FIG. 1 shows inhibition of adipocyte differentiation by coumestrol.

As used herein, "extract" means a substance extracted from a natural substance, regardless of extraction method or ingredients. The term is used in a broad sense including, for example, ingredients soluble in water or an organic solvent extracted from a natural substance using the solvent, or specific ingredients of a natural substance such as oil extracted therefrom.

Hereinafter, the present disclosure is described in further detail.

In an aspect, the present disclosure provides a composition comprising coumestrol or a bean extract comprising coumestrol as an active ingredient.

Coumestrol (CMS; 3,9-dihydroxy-6H-benzofuro(3,2-c)(1)benzopyran-6-one) has a structure of Chemical Formula 1:

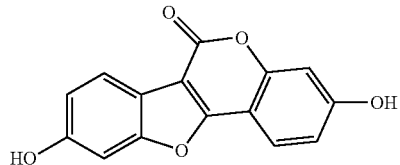

Chemical Formula 1

Coumestrol is one of phytoestrogens and is usually found in the seed, root or leaf of plants in the family Leguminosae or Compositae. It can be classified as a coumestan-like isoflavonoid and is known to have an estrogenic effect.

In an exemplary embodiment of the present disclosure, the composition comprises coumestrol, a natural substance comprising coumestrol or an extract thereof. In another exemplary embodiment of the present disclosure, the natural substance comprising coumestrol may be one or more bean selected from soybean, pea, mung bean and sprouted beans sprouted therefrom, red clover (alfalfa), Brussels sprout, or the like. In another exemplary embodiment of the present disclosure, the natural substance comprising coumestrol may be bean.

In an exemplary embodiment of the present disclosure, the bean may be any plant comprising coumestrol in the family Leguminosae, without particular limitation. For example, the bean that can be used in the present disclosure may be one for bean paste, bean curd, namul, rice cooking or green bean. The bean varieties for bean paste or bean curd include daepung, hojang, jangwon, daehwang, sodam, songhak, daewon, jinpum, danbaek, duyu, shinpaldal, taegwang, manli, jangsu, muhan, baegun, saeal, hwangkeum and jangyeop. The bean varieties for namul include shinhwa, sowon, anpyeong, seonam, dachae, sorok, soho, somyeong, dawon, pungsan-namul, iksan-namul, sobaek-namul, gwangan, danyeop and eunha. The bean varieties for rice cooking include cheongja, heukcheong, galmi, seonheuk, geomjeong-kong and ilpumgeomjeong-kong. And, the bean varieties for green bean include daol, shinrok, saeul, geomjeongeul, seokryang-putkong, hwaeom-putkong and keuneul. In another exemplary embodiment of the present disclosure, the bean may be one that can be sprouted and is resistant to damage from disease and harmful insects. Such bean varieties include, for example, shinhwa, sowon, anpyeong, seonam, dachae, sorok, soho, somyeong, dawon, pungsan-namul, iksan-namul, sobaek-namul, gwangan, danyeop and eunha.

In an exemplary embodiment of the present disclosure, the natural substance or the extract thereof may comprise a large quantity of coumestrol. Specifically, it may comprise 0.01-50 wt %, more specifically 0.1-30 wt %, of coumestrol based on the total weight of the natural substance or the extract thereof.

In an exemplary embodiment of the present disclosure, the extract of the natural substance comprising coumestrol may be obtained by extracting the natural substance comprising coumestrol with water or ethanol at normal or elevated temperature, completely concentrating the resulting extract and dispersing again in water, and fractionating with one or more solvent of equal volume selected from hexane, dichloromethane, chloroform, ethyl acetate, butanol, ethanol, methanol and water. However, the extraction method is not limited thereto and any extraction method may be employed.

In an exemplary embodiment of the present disclosure, the composition comprising coumestrol or a bean extract comprising coumestrol as an active ingredient may be a composition for inhibiting differentiation of adipocytes. Coumestrol inhibits differentiation of adipocytes and decreases mRNA expression of molecular markers of adipocyte differentiation and fatty acid synthesis. Accordingly, the composition comprising coumestrol may inhibit differentiation of adipocytes and prevent or improve obesity and various diseases induced by obesity. Examples of such diseases include type 2 diabetes, fatty liver or cardiovascular diseases, but are not limited thereto. The cardiovascular disease includes one or more of hyperlipidemia, hypertension, angina, myocardial infarction and arteriosclerosis.

In an exemplary embodiment of the present disclosure, the composition comprising coumestrol or a bean extract comprising coumestrol as an active ingredient may be a composition for enhancing immunity. Coumestrol enhances immunity and activates immune cells by proliferating the immune cells. Accordingly, the composition comprising coumestrol may enhance immunity and protect the body from microbes, bacteria, viruses, etc.

In an exemplary embodiment of the present disclosure, the composition comprising coumestrol or a bean extract comprising coumestrol as an active ingredient may be a composition for detoxifying toxic substances. The composition may detoxify toxic substances ingested into the body. Particularly, it has an excellent ability of detoxifying nicotine. Nicotine is an addiction-inducing substance contained in cigarettes and may cause negative cardiovascular effects by stimulating the sympathetic nervous system. Coumestrol increases viability of vascular endothelial cells by protecting the vascular endothelial cells from nicotine or other toxic substances. Accordingly, the composition comprising coumestrol may detoxify nicotine or other toxic substances ingested into the body and prevent or improve vascular diseases caused by the toxic substances. Examples of the vascular diseases may include blood circulation disorder, hypertension or arteriosclerosis, but are not limited thereto.

In an exemplary embodiment of the present disclosure, the composition comprising coumestrol or a bean extract comprising coumestrol as an active ingredient may be a composition for preventing or improving degenerative neurological disorders. The degenerative neurological disorders refer to the diseases occurring as a result of degenerative damage and deteriorated function of nerves or nerve cells. Examples of the degenerative neurological disorders may include glaucoma, glaucoma, myasthenia gravis, diabetic neuropathy, cerebrovascular accident, spinal cord injury, Lou Gehrig's disease (amyotrophic lateral sclerosis; ALS), Parkinson's disease, Alzheimer's disease or idiopathic dementia, but are not limited thereto. Coumestrol increases viability of nerve cells by protecting them from neurotoxins and scavenges reactive oxygen species produced by neurotoxins. Accordingly, the composition comprising coumestrol may prevent or improve degenerative neurological disorders by inhibiting the action of neurotoxins.

The composition according to an embodiment of the present disclosure may comprise 0.001-30 wt %, specifically 0.01-10 wt %, more specifically 0.1-5 wt %, of coumestrol or a bean extract comprising coumestrol based on the total weight of the composition. When the coumestrol or the bean extract comprising coumestrol is included in the above-described range, the intended effect of the present disclosure can be adequately achieved while both stability and safety are satisfied and favorable cost-effectiveness may be achieved.

In another aspect, the present disclosure provides a food composition comprising coumestrol or a bean extract comprising coumestrol. The food composition may be a health food, functional food or food additive composition.

The food composition may comprise other ingredients providing synergic effect without negatively affecting the desired effect. For example, additives such as fragrance, pigment, sterilizer, antioxidant, antiseptic, moisturizer, thickener, mineral, emulsifier, synthetic polymer, etc. may be further included. In addition, auxiliary ingredients such as water-soluble vitamin, oil-soluble vitamin, polymer peptide, polymer polysaccharide, and seaweed extract, etc. may be further included. These ingredients may be selected by those skilled in the art without difficulty considering the particular formulation or purpose of use. The addition amount may be determined within the range not negatively affecting the purpose and effect of the present disclosure.

The composition according to the present disclosure may be prepared into various formulations including solution, emulsion, viscous mixture, tablet, powder, etc.

Determination of the dose of the active ingredient is within the level of those skilled in the art. For example, the dose may be 0.1-5000 mg/kg/day, more specifically 50-500 mg/kg/day, but is not limited thereto, and may be varied with various factors including the age, physical condition, complication, etc. of a subject to be treated.

In another aspect, the present disclosure provides a pharmaceutical composition comprising coumestrol or a bean extract comprising coumestrol. The pharmaceutical composition may further comprise a pharmaceutical adjuvant such as antiseptic, stabilizer, hydrating agent, emulsifying accelerator, salt and/or buffer for controlling osmotic pressure, etc. or other therapeutically useful substance, and may be prepared into various formulations for oral or parenteral administration.

The formulation for oral administration may include, for example, tablet, pill, hard or soft capsule, liquid, suspension, emulsion, syrup, powder, dust, granule, pellet, or the like. These formulations may comprise, in addition to the active ingredient, a surfactant, a diluent (e.g., lactose, dextrose, sucrose, mannitol, sorbitol, cellulose or glycine) or a lubricant (e.g., silica, talc, stearic acid and magnesium or calcium salt thereof or polyethylene glycol). The tablet may comprise a binder such as magnesium aluminum silicate, starch paste, gelatin, tragacanth, methyl cellulose, sodium carboxymethyl cellulose and polyvinylpyrrolidone, and may occasionally comprise a pharmaceutical additive such as a disintegrant, e.g. starch, agar, alginic acid or a sodium salt thereof, an absorbent, a colorant, a flavor, a sweetener, or the like. The tablet may be prepared according to the commonly employed mixing, granulation or coating method.

The formulation for parenteral administration may include, for example, injection, drop, ointment, lotion, gel, cream, spray, suspension, emulsion, suppository, patch, etc., but is not limited thereto.

A pharmaceutically acceptable amount, i.e. administration dose, of the dose of the active ingredient will vary depending on the age, sex and body weight of the subject to be treated, severity of particular disease or pathological condition to be treated, administration route and discretion of the prescriber. Those skilled in the art may determine the administration dose considering the known bioavailability of coumestrol upon oral administration (about 11.7%) as well as the above-described factors. For example, a general administration dose may be 0.01-1000 mg/kg/day, specifically 1-40 mg/kg/day. However, the described administration dose does not limit the scope of the present disclosure by any means.

The features and effects of the present disclosure will be described in detail through test examples. However, the following test examples are provided for illustrative purposes only and are not intended to limit the scope of the present disclosure.

[Test Example 1] Evaluation of effect of Inhibiting Adipocyte Differentiation

In order to evaluate the coumestrol's effect of inhibiting adipocyte differentiation, 10 M coumestrol (CMS) was administered continuously while 3T3-L1 mouse preadipocytes (CL-173, ATCC) were differentiated into adipocytes. 1 M Rosiglitazone (Rosi), which is known to promote adipocyte differentiation, was used as positive control and 10 M berberine (BBR), which is known to inhibit adipocyte differentiation, was used as negative control. On the day when adipocyte differentiation was started and on days 2, 4 and 6, the test substance was administered and the medium was changed. The adipocyte differentiation was carried out for about 7 days when the adipocyte differentiation was completed in the positive control group.

Then, differentiation of adipocytes was identified by staining triglycerides in the cells with Oil Red O (Sigma). The result is shown in FIG. 1. As seen from FIG. 1, the group treated with coumestrol showed less stained area than those treated with the positive control rosiglitazone or the negative control berberine. This means that adipocyte differentiation is remarkably decreased by coumestrol and the effect is superior to that of berberine.

Figure 2:
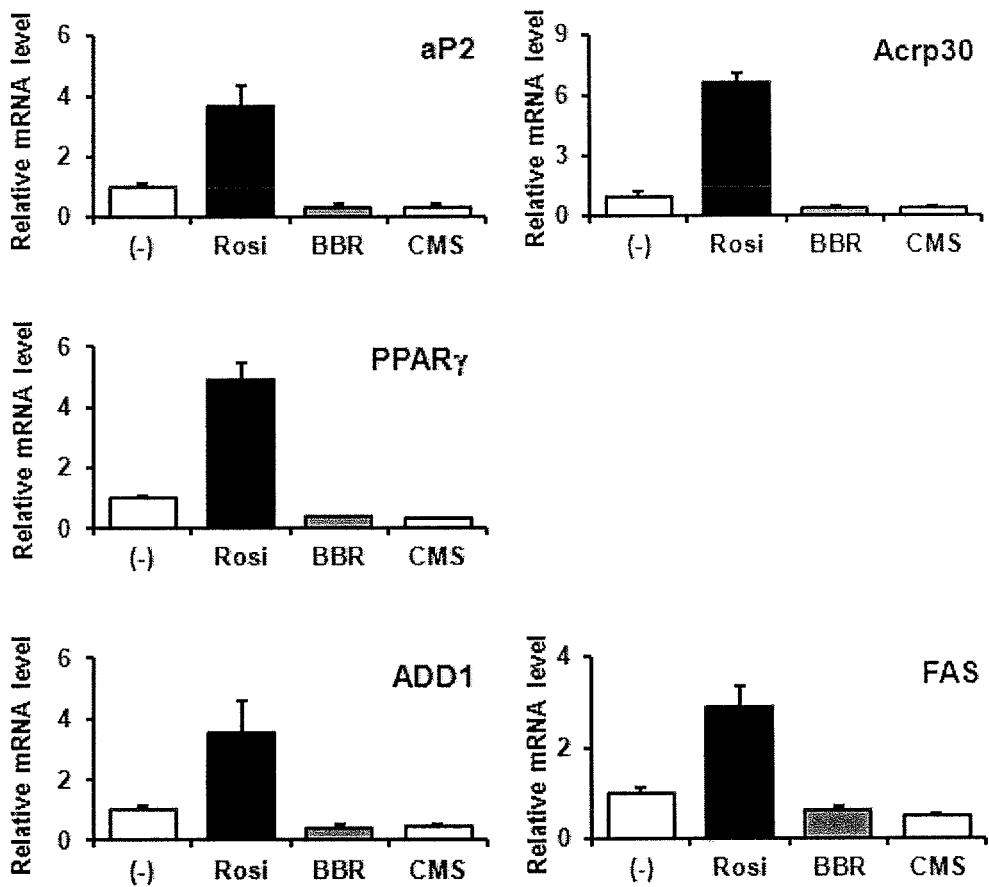
FIG. 2 shows decreased expression of adipocyte marker genes by coumestrol.

Also, expression of adipocyte-specific genes in the in the adipocytes was investigated by Q-PCR. The expression level of each group relative to the untreated group was evaluated and is shown in FIG. 2. The genes tested were aP2 (fatty acid binding protein 4, adipocyte specific type), Acrp30 (adiponectin), PPAR (peroxisome proliferator-activated receptor), SREBP1c (sterol regulatory element binding protein 1c) and FAS (fatty acid synthase), which are used as molecular markers of adipocyte differentiation and fatty acid synthesis. As seen from FIG. 2, coumestrol resulted in remarkably decreased mRNA expression of the molecular markers of adipocyte differentiation and fatty acid synthesis, and the effect was better than that of berberine.

Thus, coumestrol inhibits adipocyte differentiation and fatty acid synthesis. Accordingly, the composition comprising coumestrol may prevent or improve obesity and may prevent or improve type 2 diabetes, fatty liver, cardiovascular disease, etc. caused by obesity.

[Test Example 2] Evaluation of Immune Cell Activating Effect

Spleen was aseptically removed from an ICR mouse sacrificed by cervical dislocation. The spleen was washed with an RPMI 1640 solution and lightly smashed with a sterilized glass rod to isolate the mouse spleen cells. A suspension of the isolated cells was passed through a 200-mesh stainless steel sieve (Sigma Chemical Co., St. Louis, Mo., USA) and centrifuged for 10 minutes at 4° C. and 3,000 rpm in a 50-mL centrifuge tube. The resulting cell pellets were suspended in a lysing buffer (Tris-buffered ammonium chloride; 0.87% $NH_4Cl$, pH 7.2) for 5 minutes to remove red blood cells. The cells were washed twice with RPMI by centrifugal washing, diluted to $5.0 \times 10^6$ cells/mL in 10%-FBS RPMI 1640, and seeded on a 96-well plate, with 90 μL per each well, for measurement of cell proliferating activity. After preparing a stock solution such that the final concentration of coumestrol was 0.1 or 1 μM and adding 10 μL to each well, the cells were cultured for 44 hours and the proliferating activity of the spleen cells was measured (CCK-8, Dojindo Laboratories, Japan). 10 μL of 10 μg/mL LPS was used as positive control. The immune cell proliferating activity (%) of each group relative to the untreated group was measured and is shown in Table 1.

TABLE 1

|  | Immune cell proliferating activity (%) |
| --- | --- |
| Untreated | 100 |
| LPS, 10 μg/mL (positive control) | 275 |
| Coumestrol, 0.1 μM | 278 |
| Coumestrol, 1 μM | 283 |

As seen from Table 1, coumestrol promotes proliferation of immune cells, and the effect is better than that of the positive control at higher concentration. Accordingly, the composition comprising coumestrol may provide a superior effect of enhancing immunity by activating immune cells.

[Test Example 3] Evaluation of Nicotine Detoxifying Effect

Human umbilical vein endothelial cells (HUVECs, CRL-2873, ATCC) were used to evaluate the coumestrol's effect against nicotine which is a major toxic substance included in cigarettes. HUVECs were cultured under the condition of 37° C. and 5% $CO_2$ using the microvascular endothelial cell growth medium-2 (EGM-2). The cells were seeded onto a 96-well plate, with $2 \times 10^4$ cells per well, and cultured for about 24 hours in a medium containing 10% FBS until ~80% confluency. After treating with nicotine to a final concentration of 25 mM, the cells were cultured for 24 hours with 0.1, 1 or 10 μM coumestrol, except for the negative control group. The viability (%) of the vascular endothelial cells was evaluated relative to the untreated group and is given in Table 2.

TABLE 2

| | Viability of vascular endothelial cells (%) |
|---|---|
| Untreated | 100 |
| Negative control | 55.1 |
| Coumestrol, 0.1 μM | 67.2 |
| Coumestrol, 1 μM | 72.2 |
| Coumestrol, 10 μM | 88.9 |

As seen from Table 2, coumestrol increases the viability of vascular endothelial cells by detoxifying nicotine. Accordingly, the composition comprising coumestrol may detoxify toxic substances ingested into the body and prevent or improve vascular diseases caused thereby.

[Test Example 4]Evaluation of Effect of Inhibiting Neurotoxins

1. Evaluation of Effect of Protecting Nerve Cells from Neurotoxins

SH-SY5Y cells (CRL-2266, ATCC) were used to evaluate the coumestrol's effect of protecting nerve cells from neurotoxins. The cells were cultured in a medium comprising 90% DMEM, 10% fetal calf serum, 100 IU/mL penicillin and 100 μg/mL streptomycin under the condition of 37° C. and 5% $CO_2$. When the cells grew confluent, they were harvested with trypsin, diluted on a 96-well plate to $1 \times 10^4$ cells per well, and then grafted onto a culture dish. 24 hours later, after treating the cultured cells with 0.01, 0.1 or 1 μM coumestrol, the cells were treated with 50 μM 6-OHDA 2 hours later to induce cytotoxicity. A negative control group was treated only with 50 μM 6-OHDA. The viability (%) of the nerve cells was measured by MTT assay 24 hours later and the result is shown in Table 3. Also, mitochondrial potential of the cells was measured using the JC-1 fluorescent reagent (Beyotime, China). The effect of inhibiting decline of mitochondrial potential (%) is shown in Table 4.

TABLE 3

| | Viability of nerve cells (%) |
|---|---|
| Untreated | 100 |
| Negative control (50 μM 6-OHDA) | 78.6 |
| Coumestrol, 0.01 μM | 94.4 |
| Coumestrol, 0.1 μM | 96.5 |
| Coumestrol, 1 μM | 98.2 |

TABLE 4

| | Effect of inhibiting decline of mitochondrial potential (%) |
|---|---|
| Negative control (50 μM 6-OHDA) | 0 |
| Coumestrol, 0.01 μM | 13.2 |
| Coumestrol, 0.1 μM | 29.1 |
| Coumestrol, 1 μM | 43.0 |

As seen from Tables 3 and 4, coumestrol increases the viability of nerve cells in the presence of neurotoxins and has an excellent effect of inhibiting decline of mitochondrial potential.

2. Evaluation of Effect of Scavenging Reactive Oxygen Species Produced by Neurotoxins The same cells used in Test Example 4-1 were cultured under the same condition. The cultured cells were treated with 0.01, 0.1 or 1 μM coumestrol and then treated with 50 μM 6-OHDA 2 hours later to induce increase of reactive oxygen species (ROS) in the cells. After culturing the cells for 6 hours in an incubator, the quantity of ROS in the cells was measured using DCFH-DA and the decrease of the ROS was evaluated relative to the negative control group. The fluorescence intensity of DCF was measured with the Wallac VICTOR2 fluorometer (Wallac, Turku, Finland) at excitation wavelength of 485 nm and emission wavelength of 530 nm. ROS scavenging effect (%) relative to the negative control group was calculated from the measured fluorescence intensity. The result is given in Table 5.

TABLE 5

| | ROS scavenging effect (%) |
|---|---|
| Negative control (50 μM 6-OHDA) | 0 |
| Coumestrol, 0.01 μM | 73.0 |
| Coumestrol, 0.1 μM | 86.7 |
| Coumestrol, 1 μM | 93.5 |

As seen from Table 5, coumestrol has an excellent effect of scavenging ROS produced by neurotoxins.

Accordingly, the composition comprising coumestrol may prevent or improve degenerative neurological disorders by inhibiting the action of neurotoxins.

Formulation examples of the composition according to the present disclosure are described hereinafter. However, the scope of the present disclosure is not limited to the following examples.

[Formulation Example 1]Soft Capsule

Coumestrol (80 mg), vitamin E (9 mg), vitamin C (9 mg), palm oil (2 mg), hydrogenated vegetable oil (8 mg), yellow beeswax (4 mg) and lecithin (9 mg) are mixed and prepared into a soft capsule filling solution according to a commonly employed method. 400 mg of the solution is filled per capsule. Separately from this, a soft capsule sheet is prepared using gelatin 66 (wt %), glycerin (24 wt %) and sorbitol (10 wt %), which is filled with the filling solution to prepare a soft capsule containing 400 mg of the composition according to the present disclosure.

[Formulation Example 2]Tablet

Coumestrol (80 mg), vitamin E (9 mg), vitamin C (9 mg), galactooligosaccharide (200 mg), lactose (60 mg) and maltose (140 mg) are mixed and granulated using a fluidized bed dryer. After adding sugar ester (6 mg), the resulting composition (500 mg) is prepared into a tablet according to a commonly employed method.

[Formulation Example 3]Drink

Coumestrol (80 mg), vitamin E (9 mg), vitamin C (9 mg), glucose (10 g), citric acid (0.6 g) and oligosaccharide syrup (25 g) are mixed. After adding purified water (300 mL), 200 mL of the resulting mixture is filled in a bottle. Then, a drink is prepared by sterilizing at 130° C. for 4-5 seconds.

[Formulation Example 4]Granule

Coumestrol (80 mg), vitamin E (9 mg), vitamin C (9 mg), anhydrous crystalline glucose (250 mg) and starch (550 mg) are mixed, granulated using a fluidized bed granulator, and then filled in a pouch.

[Formulation Example 5] Injection

| Coumestrol | 20 mg |
|---|---|
| Sterilized distilled water for injection | adequate |
| pH adjuster | adequate |

An injection is prepared using the above ingredients per ampule (2 mL) according to a commonly employed method.

Those skilled in the art will appreciate that the present disclosure may be changed and modified variously within the scope of the present disclosure.

The invention claimed is:

1. A method for inhibiting the action of 6-hydroxydopamine (6-OHDA) against nerve cells, comprising administering a therapeutically effective inhibiting amount of coumestrol or a bean extract comprising coumestrol to a subject in need thereof in a dose greater than 50 mg/kg/day based on the coumestrol, wherein the coumestrol or the bean extract comprising coumestrol is administered in the form of a health food or pharmaceutical composition.

2. The method of claim 1, wherein inhibiting the action of 6-hydroxydopamine against the nerve cells improves a degenerative neurological disorder comprising one or more of dementia, Alzheimer's disease and Parkinson's disease.

3. The method of claim 1, wherein the dose is up to 5000 mg/kg/day.

4. The method of claim 3, wherein the dose is up to 500 mg/kg/day.

5. The method of claim 1, comprising administering a bean extract wherein coumestrol is present in the bean extract in an amount of about 0.1 to about 50 percent by weight.

6. The method of claim 5, comprising administering a bean extract wherein coumestrol is present in the bean extract in an amount of about 0.1 to about 30 percent by weight.

* * * * *